United States Patent [19]

Stewart

[11] Patent Number: 5,020,522
[45] Date of Patent: Jun. 4, 1991

[54] COMPACT VACUUM THERAPY SYSTEM

[76] Inventor: Edward T. Stewart, 107 Plaza Ter., Dodge City, Kans. 67801

[21] Appl. No.: 490,465

[22] Filed: Mar. 8, 1990

[51] Int. Cl.⁵ .............................................. A61F 5/00
[52] U.S. Cl. ...................................................... 128/79
[58] Field of Search ......................................... 128/79

[56] References Cited

U.S. PATENT DOCUMENTS

| | | | |
|---|---|---|---|
| 1,498,430 | 6/1924 | Doerfler | 128/79 |
| 2,614,565 | 10/1952 | Packer | 128/327 |
| 2,874,698 | 2/1959 | Sell | 128/79 |
| 3,421,504 | 1/1969 | Gibbons | 128/79 |
| 3,631,853 | 1/1972 | Burdette | 128/79 |
| 3,744,486 | 7/1973 | Wilson | 128/79 |
| 4,175,554 | 11/1979 | Gerow | 128/79 |
| 4,718,411 | 1/1988 | Stewart | 128/79 |
| 4,741,329 | 5/1988 | Marcune | 128/79 |
| 4,753,227 | 6/1988 | Yanuck, Jr. | 128/79 |
| 4,856,499 | 8/1989 | Kelly | 128/79 |

FOREIGN PATENT DOCUMENTS 148586 7/1985 European Pat. Off. .
774558 10/1980 U.S.S.R. .

Primary Examiner—Cary E. Stone
Attorney, Agent, or Firm—Hovey, Williams, Timmons & Collins

[57] ABSTRACT

A compact vacuum therapy system useful in the treatment of male sexual dysfunction is provided which includes a pump body which is designed for removable mounting on a tube in both storage and operational positions. The pump body includes a reciprocable piston having a circumscribing groove of a width to permit axial shifting of an O-ring sealing member therewithin during movement of the piston within the pump body. The shifting sealing member thus acts as a valve to alternately seal and open a slot defined in the piston transverse to the groove during the reciprocating strokes of the piston. The piston is axially oriented with the intake and the tube when the pump body is mounted to the tube.

9 Claims, 3 Drawing Sheets

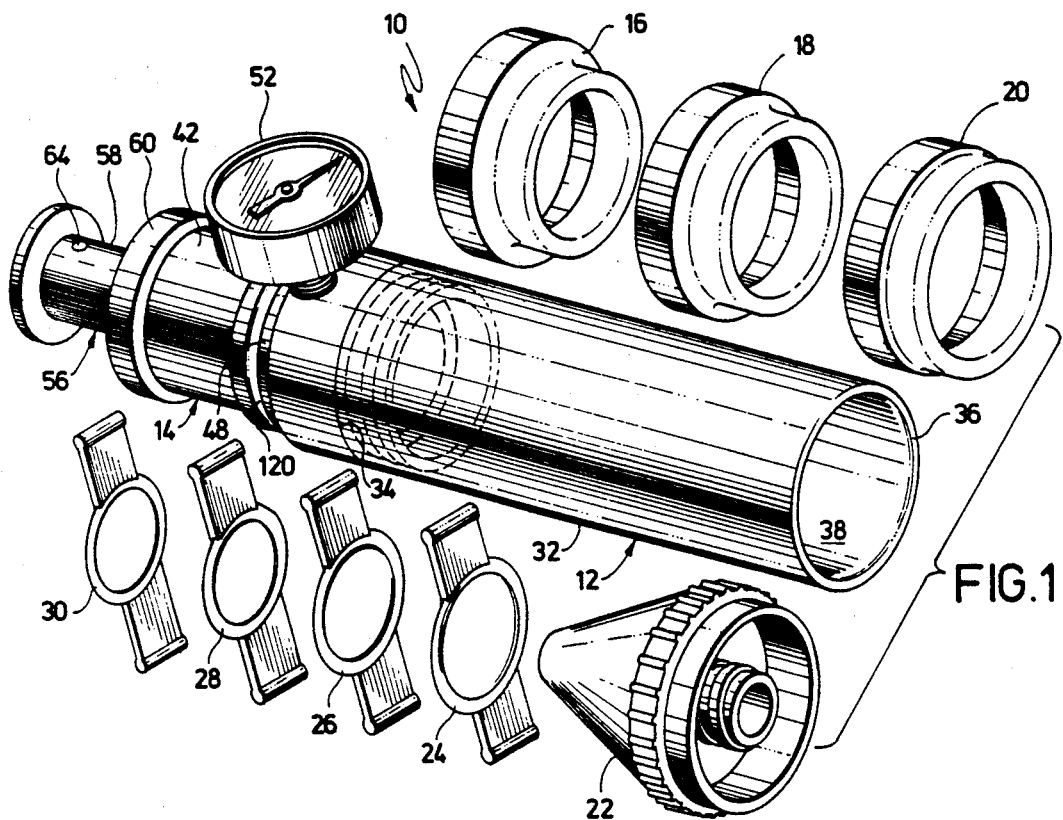
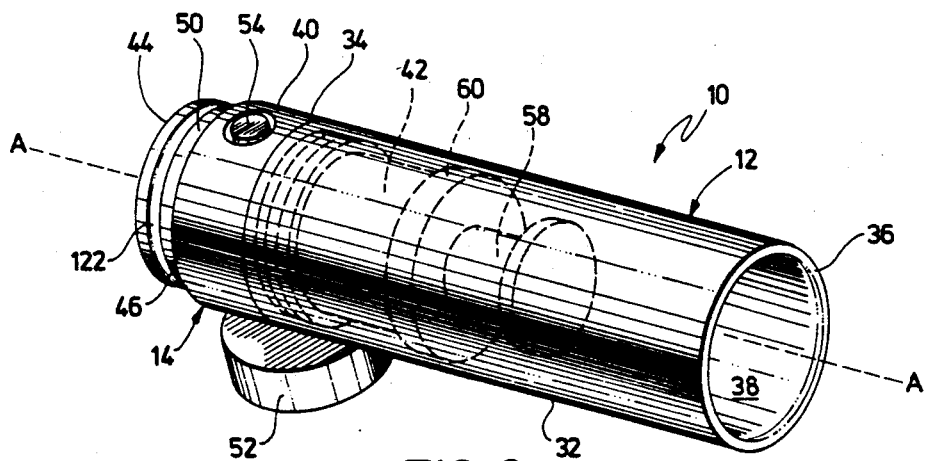

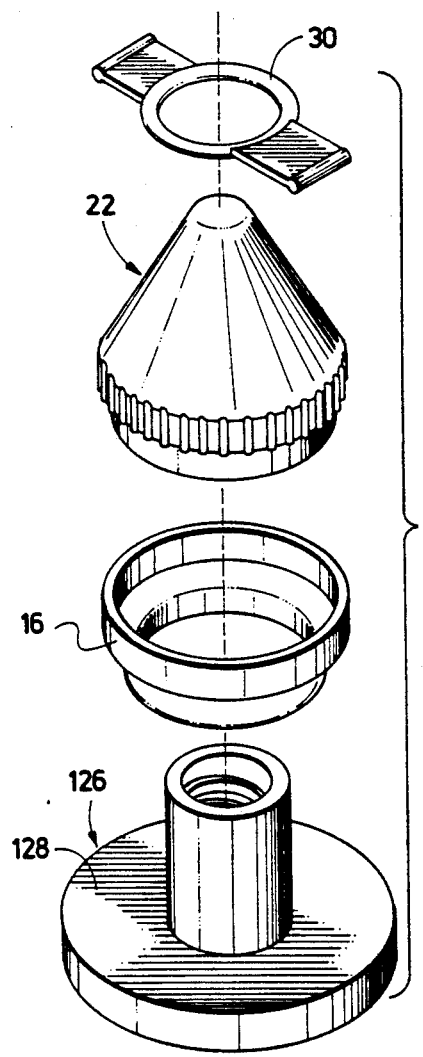
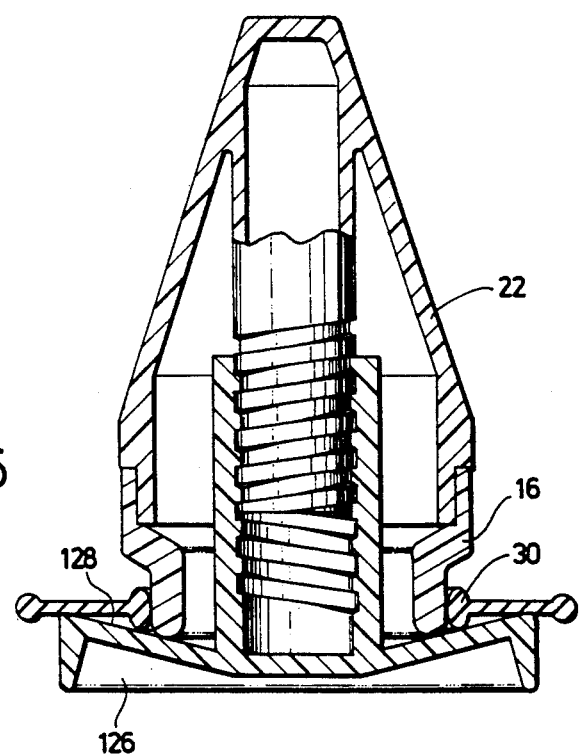
FIG. 6
FIG. 7

COMPACT VACUUM THERAPY SYSTEM

BACKGROUND OF THE INVENTION

1. Field of the Invention

The present invention is concerned with a vacuum therapy system for use in treatment of male sexual dysfunction which is compactly constructed for ease of use and storage. The pump piston is actually oriented with respect to a penile receiving tube whereby the pump body may be mounted in either an operating or storage position, and the pump piston presents an efficient structure for obtaining and maintaining a vacuum within a tube adapted for receiving a male organ therewithin.

2. Description of the Prior Art

A variety of different devices and methods have been utilized to treat male sexual dysfunction in those men who have difficulty in producing an erection in a normal manner. Included in this field are those devices which include a tube which is large enough to contain the erected penis and adapted to be sealed around the penis when it is not erect, as well as a pump operable to evacuate air from the tube to produce a partial vacuum around the penis. The evacuation of air from within the tube causes blood to flow into the vessels of the male organ and engorge the penis under normal blood pressures. Thus, the additional supply of blood produces an erection. In some instances, it may be necessary to employ a constrictor band around the base of the penis in order to maintain the erection after it has been produced.

A variety of different devices for producing an erection by vacuum therapy have been known in the art, including prior U.S. Pat. No. 4,718,411 which issued Jan. 12, 1988. While these devices have generally been effective in producing a vacuum within a tube adapted to receive the male organ, they have sometimes proven cumbersome and difficult to use. The size and weight of the pump apparatus have made them difficult to manipulate in use, and in fact have been of such a scale as to be somewhat frightening to the user or his partner. Moreover, the sheer size and weight of these units have made movement and storage sometimes difficult. The size and configuration of these units has additionally made it difficult to pack such apparatus in suitcases for use during travel. As such, there has developed a need for a compact, easily storable, simple to use vacuum therapy device which can be economically manufactured and easily manipulated in use.

SUMMARY OF THE INVENTION

The problems outlined above are in large measure solved by the compact vacuum therapy system in accordance with the present invention which is easily storable, efficient to use and economical to manufacture. The structure hereof is advantageously of a compact nature while still providing the safety features necessary to reduce the likelihood of injury to the patient.

The vacuum therapy system in accordance with the present invention broadly includes a pump body and a tube which are cooperatively sized and configured so that the pump body may be mounted at either its intake end or its piston-receiving end to the tube. The pump body includes a reciprocable piston located within its piston-receiving end which is axially oriented with the intake end. The intake end is adapted to receive air to be evacuated from the penile tube and convey it downstream towards the piston-receiving end of the pump body.

The configuration of the pump body itself efficiently includes both manually operated and automatically opening relief valves, as well as a unique check-valve structure. Intermediate the piston-receiving end and the intake end is a circumscribing rim which mounts both a manually actuatable relief valve for admitting air into the penile tube and a vacuum gauge for monitoring the amount of vacuum within the penile tube. The portion of the pump body interior to the rim defines a plenum which is divided from the piston-receiving portion by a wall. The wall includes an aperture for receiving a one way check valve, while on the opposite or downstream side of the wall is a piston which is biased outwardly by a spring.

The piston includes a circumscribing groove. The groove receives an O-ring sealing member between the groove and the surrounding wall of the pump body, the groove being sufficiently wide to permit axially shifting of the O-ring during reciprocating strokes of the piston. At least one opening is provided in the rear wall of the piston, the opening lying in communication with a trench which is oriented transversely to the groove. By this construction, the O-ring moves rearwardly during the inward pump stroke, thereby allowing air to pass through the slot and out the passageway into the atmosphere, while when the piston is biased rearwardly by the spring, the O-ring moves forwardly with respect to the piston and seals against the front wall of the groove and prevents the passage of air into the plenum and tube.

The piston also includes a novelly arranged vacuum relief valve which is axially oriented within the piston. A plug is spring biased rearwardly against a sealing member to prevent the passage of air through the piston and into the plenum unless the pressure differential between the ambient atmosphere and the plenum is such as to cause the air pressure to overcome the spring tension.

The device hereof may include various sealing rings and constrictor ring adapters for use in conforming the device to the male user. The pump body may be easily separated from the tube and stored with the piston-receiving end of the pump body interior to the tube. In preferred embodiments, O-rings are located in groove surrounding shoulders adjacent the rim for holding the tube in place and maintaining an airtight connection between the tube and the pump body.

BRIEF DESCRIPTION OF THE DRAWINGS

FIG. 1 is a perspective view of the compact vacuum therapy system of the present invention, showing the penile tube mounted at the intake end of the pump body and showing various adaptor sleeves and constriction rings and a mounting cone for use therewith;

FIG. 2 is a perspective view of the tube and pump body of the present invention showing the pump body reversed on the tube and oriented in a storage position;

FIG. 6 is an exploded perspective view of the mounting cone and a mounting base, with a sleeve and constrictor ring also shown in the disassembled position; and FIG. 7 is a vertical cross sectional view of the mounting cone and base assembly as constructed in use.

DETAILED DESCRIPTION OF THE DRAWINGS

Figures 3A, 3B:
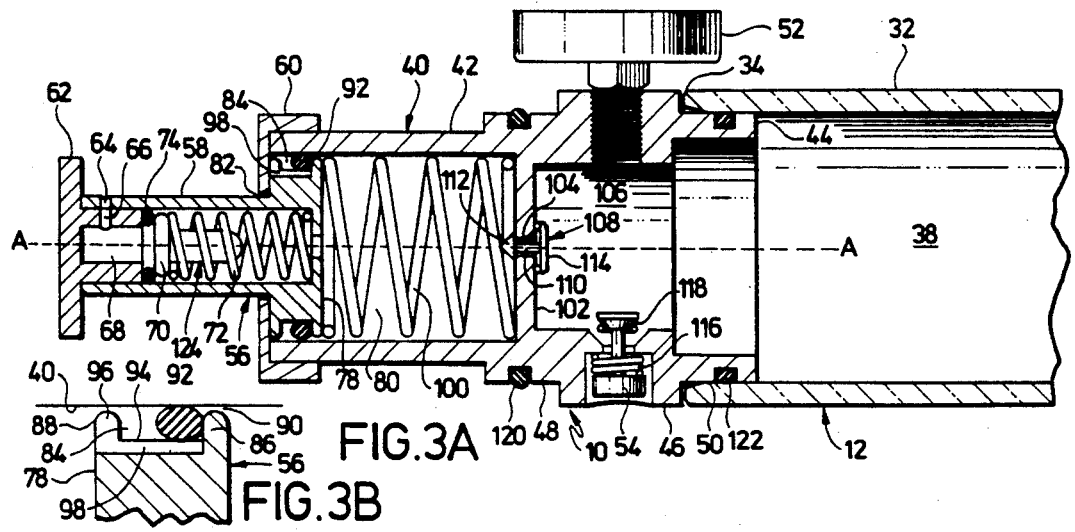
FIG. 3A is an enlarged, fragmentary cross sectional view of the compact vacuum therapy system hereof taken through the center of the pump body and tube showing the manually actuated and automatic relief valves, as well as showing the check valve and the piston when in a stationary, unevacuated condition.
FIG. 3B is an enlarged, fragmentary view of the groove and O-ring of the piston in FIG. 3A showing the groove walls and slot therein.

Referring now to the drawing, a compact vacuum therapy system 10 is shown in FIG. 1 and broadly includes an elongated tube 12, a vacuum pump unit 14, a series of alternately mountable resilient adapter sleeves 16, 18 and 20 for attachment to a tube 12 opposite pump unit 14, a constrictor ring mounting cone 22 and a series of selectively sized elastic constrictor rings 24, 26, 28 and 30. Mounting cone 22 is configured to receive one of the constrictor rings 24, 26, 28 or 30 thereon in expanded orientation for transfer of the selected constrictor ring over the desired adapter sleeve prior to the initiation of therapy.

In somewhat greater detail, tube 12 includes a cylindrical wall 32 defining a pump receiving first end 34, an adapter sleeve mounting second end 36 and a chamber 38 extending therebetween sized for receiving a male organ therein. In the preferred embodiment, the wall 32 is constructed of a clear material such as a clear synthetic resin material to permit examination of the male organ during operation and is substantially cylindrical, but it may be appreciated that other shapes could be employed. In the embodiment set forth and shown herein, pump 14 and adapter sleeves 16, 18 and 20 may be mounted on either end 34 or end 36 of tube 12.

Pump unit 14 broadly includes a pump body 40 having a piston receiving end 42 and an intake end 44. A rim 46 is positioned intermediate receiving end 42 and intake end 44 and is raised relative to adjacent shoulder surfaces 48 and 50 located adjacent piston-receiving end 42 and intake end 44, respectively. Rim 46 is bored and threaded to receive a vacuum gauge 52 thereon. In addition, a manually relief button 54 is located in rim 46 as best seen in FIG. 2. When depressed, relief button 54 actuates a relief valve to admit air into tube 12.

Figures 4A, 4B:
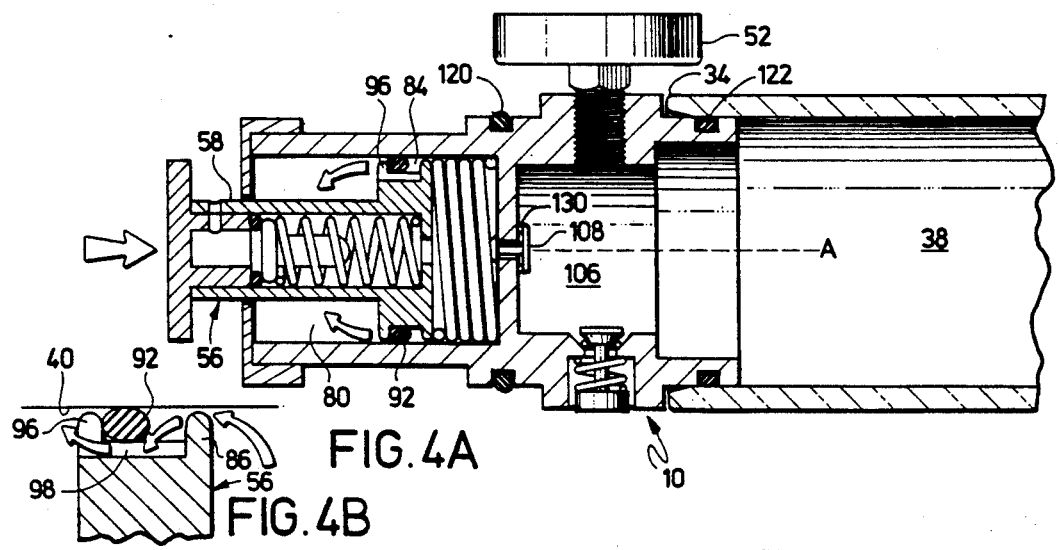
FIG. 4A is a view similar to FIG. 3A showing the operation of the pump during an inward stroke of the piston and the movement of air by curved arrows.
FIG. 4B is a view similar to FIG. 3B showing the orientation of the O-ring within the groove during an inward stroke, and the passage of air through the trench and opening shown by curved arrows.
Figures 5A, 5B:
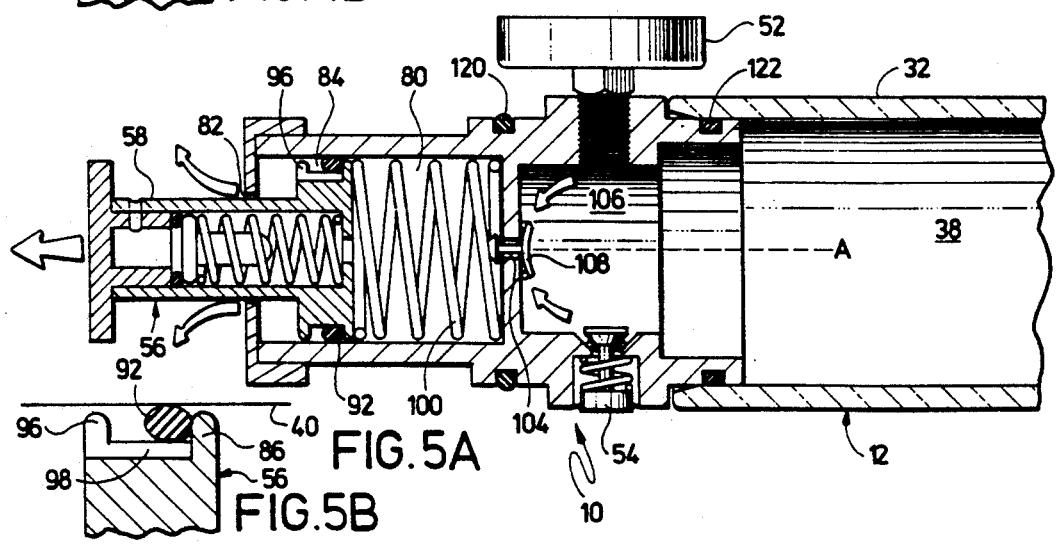
FIG. 5A is a view similar to FIG. 3A but showing the internal components of the invention hereof during the outward stroke of the piston with the movement of air shown by curved arrows.
FIG. 5B is a view similar to FIG. 4B but showing the positioning of the O-ring sealing member against the front wall of the groove during the outward stroke of the piston.

Pump body 40 is oriented along a longitudinal axis A as may be seen in FIGS. 3A, 4A and 5A which is coaxial with tube 12 when mounted in either an operational or storage orientation. A piston 56 includes a hollow shaft 58 which projects outwardly through cap 60 secured onto pump body by friction fit, or alternatively by adhesive or threading. The shaft 58 is essentially tubular and receives a base 62 thereon. Base 62 is provided with a port 64 which is in registry and fluid communication with an airway 66 in shaft 58.

Referring now to FIG. 3A, showing the tube 12, pump body 40, piston 56, cap 60 and base 62 is cross section, it may be seen that port 64 on shaft 58 provides a means for air to enter airway 66 and into hollow 68 in the base 62. Plug 70 is normally biased rearwardly by regulator spring 72 against an O-ring 74 in airtight relationship. O-ring 74 provides a seal against shaft 58 and base 62 and lies in engagement with plug 70 when the atmospheric pressure of the ambient air exterior to pump 14 is insufficient to overcome the biasing force of spring 72 against plug 70. A hole 76 is defined in the head 78 of piston 56 for the passage of air into bore 80 in the event such resistance is overcome.

Shaft 58 of piston 56 is of a somewhat smaller diameter than aperture 82 in cap 60 through which the shaft passes, and the resulting clearance is sufficient to enable the passage of air between cap 60 and shaft 58. Shaft 58 and piston head 78 are preferably integrally formed of a rigid synthetic resin material, with pump body 40, cap 60 and base 62 formed of the same material.

Referring now to FIG. 3B, head 78 of piston 56 is preferably essentially discoidal in shape and presents a circumscribing groove 84 defined by a front wall 86 and a rear wall 88. The diameter of head 78 presents an annular space 90 between both front wall 86 and rear wall 88 and pump body 40. An O-ring sealing member 92 of neoprene or other suitable synthetic resin material is positioned in groove 84 and sized to effect a seal between bottom wall 94 and pump body 40. Groove 84 is of a sufficient width to enable O-ring 92 to shift axially during reciprocation of the piston 56.

At least one opening 96 is defined in the rear wall 88, the opening fluidically communicating with a trench 98 which is axially aligned and transversely oriented with respect to groove 84. The trench 98 is of sufficient depth to enable air to pass beneath O-ring 92. The opening 96 and trench 98 are aligned so that air moving through trench 98 is able to pass through opening 96. A plurality of such openings 96 and trenches 98 may be provided at circumferentially spaced intervals around rear wall 88.

A return spring 100 is located in bore 80 between partition wall 102 and piston head 78 for urging piston 56 rearwardly. A circular slot 104 is defined in the center of partition wall 102 for placing bore 80 in fluidic communication with plenum 106. A check valve 108 is positioned in slot 104 and includes a stem 110, a conical head 112 and a circular back 114. The stem is of slightly greater length than the thickness of partition wall 102 to permit limited movement of the check valve 108 in an axial direction and stem 110 is of a sufficiently smaller diameter than slot 104 to permit the passage of air therearound. A series of nibs 130 are located at spaced intervals on back 114 to provide an air path between back 114 and wall 102. Check valve 108 is made of urethane or other resilient material.

Relief button 54 is located in a recess within rim 46 and is biased outwardly by spring 116 to maintain valve 118 adjacent to pump body 40 unless overcome by external force. Tube 12 is retained on pump body 40 by virtue of the fit between the internal diameter of tube wall 32 and either shoulder 48 or shoulder 50. O-rings 120 and 122 are located in circumscribing grooves in shoulders 48 and 50 for holding the tube in position on pump body 40 and to effect an airtight seal therebetween.

Prior to operation of the compact vacuum therapy system 10, the user assembles an appropriately sized adapter sleeve 16, 18, 20, with one of the constrictor rings 24, 26, 28, 30, in a manner as illustrated in FIG. 6. Initially, the chosen sleeve is fitted over the enlarged end of the mounting cone 22, with the reduced diameter end of the sleeve located remote from the cone. Thereafter, the cone is secured to a mounting base 126 by turning the cone and sleeve assembly onto the base such that an outer threaded section of the cone engages an inner threaded section of the base.

Once the cone 22 and sleeve 16, 18 or 22 have been secured to the base, one of the constrictor rings 24, 26, 28, 30 is urged onto the mounting cone 22 as shown in FIG. 6, and is worked over the surface of the cone and is stretched to a diameter sufficient to pass over the cone and onto the sleeve. The ring 24, 26, 28 or 30 is then worked completely along the length of the ring until positioned in the location shown in FIG. 7, with the ring disposed a slight distance above the lower axial end of the sleeve. A viscous lubricating jelly may aid in transferring the constrictor ring onto the sleeve.

The mounting base 126 includes an upper surface 128 having a slight angle relative to the horizontal so that when one of the rings 24, 26, 28 or 30 is assembled on one of the sleeves 16, 18 or 20, the ring is maintained in a position slightly distanced from the end of the sleeve. By ensuring that the ring is so located, the possibility of the ring sliding from the sleeve prematurely upon removal of the sleeve from the cone is reduced and use of the apparatus is simplified.

After the constrictor ring 24, 26, 28 or 30 has been assembled on the chosen sleeve, the cone 22 is unscrewed from the mounting base 126 and the sleeve and ring are disassembled from the cone. Thereafter, the sleeve and ring are fitted to the end of the tube 12, with the small diameter end of the sleeve located remote from the tube 1.

In use, the patient or user places his penis inside tube 12 and effects a seal between the selected adapter sleeve and the base of the penis. The patient or user then actuates the piston 56 by pushing on base 62 to produce several reciprocating strokes of the piston. As the piston 56 is actuated, air is evacuated from tube 12 and the penis becomes engorged with blood. If an erection is achieved, the patient or user may depress relief button 54, as shown in FIG. 3A, to admit air into plenum 106 and chamber 38, thus relieving the vacuum therewithin. If an erection is maintained, the user or patient withdraws his penis from the tube 12 and proceeds with intercourse, but if the erection is not otherwise maintainable, the selected constrictor ring is transferred from the adapter sleeve to the base of the user's penis prior to withdrawal from the tube 12.

The system 10 may then be stored by separating the tube 12 from the pump unit 14. Whereas the tube 12 is mounted on shoulder 50 of pump body 40 with intake end 44 interior to tube 12 during use, the system 10 is stored with the pump body 40 reversed with respect to tube 12. Thus, in the storage position, tube 12 is mounted on shoulder 48 of pump body 12 with piston 56 and piston-receiving end 42 interior to tube 12. As may be readily apparent from a comparison of FIG. 1 and 2, the ability to store pump unit 14 with piston-receiving unit 42 interior to tube 12 as shown in FIG. 2 produces a more compact arrangement than the operating orientation of FIG. 1.

It may also be appreciated that the axial alignment of the base, piston, piston-receiving end and intake end with tube 12 results in a simplified and more compact system 10 than those of the prior art. This is accomplished while retaining the necessary safety features of both a manually actuatable relief valve 118 and a vacuum overload regulator 124 comprising hollow 68, O-ring 74, plug 70, port 64, airway 66, spring 72 and hole 76. By positioning the vacuum overload unit 124 substantially within shaft 58 and base 62, substantial space savings are achieved.

The internal evacuating operation of the pump unit 14 may best be viewed in FIGS. 4A, 4B, 5A and 5B. In order to evacuate chamber 38, the user pushes inwardly on base 62 to move the piston toward partition wall 102 or to the right as shown in FIG. 4A. As the piston 56 moves to the right, the O-ring sealing member 92 shifts relatively axially to the left in groove 84, as shown in FIG. 4B. The O-ring 92 thus is no longer in abutment with front wall 86, permitting air from bore 80 to move into trench 98 and out through opening 96 in rear wall 88. The air is thus moved from the front or right of piston 56 to the left or rear. The air is prevented from moving to the right through slot 104 by head 112 of check valve 108 which blocks slot 104 as the piston 56 pushes the air in bore 80 against the head 112.

Upon completion of the inward stroke of piston 56, it is then returned to the rearward or leftmost position shown in FIG. 3A by return spring 100. Referring now to FIG. 5A, as the piston 56 moves to the left, O-ring sealing member 92 moves axially within groove 84 to the position shown in FIG. 5B. In this position, the O-ring 92 seals against front wall 86 to prevent air from entering trench 98. The air previously in bore 80 is thus expelled through aperture 82, as shown by the curved arrows in FIG. 5B. Additionally, air from chamber 38 is drawn in around back 114 of check valve 108. As piston 56 is reciprocated outwardly by return spring 100, head 112 moves out of slot 104. Back 114 is prevented from sealing off slot 104 by nibs 126 at spaced intervals on back 114. Thus, air from chamber 38 and plenum 106 moves around back 114 and nibs 126 to pass through slot 104 and enter bore 80.

Through a succession of reciprocations of piston 56, tube 12 can be evacuated to achieve successful engorgement of the penis of the user or patient. With each successive stroke, additional air is withdrawn from chamber 38. A system 10 of the present type is capable of achieving a vacuum of 5 inches Hg in three to five reciprocations and 10 inches Hg in 10 to 15 reciprocations. A vacuum in excess of 12 inches Hg should normally be avoided to prevent rupture of the penile blood vessels, and an excessive vacuum will result in air leaking into bore 80 through vacuum overload unit and then gradually passing through slot 104.

It is to be understood that the foregoing description sets forth the preferred embodiment of my invention and that a variety of alterations and minor modifications may be made without departing from the spirit of the invention. Accordingly, the scope of my invention should be determined by the claims as set forth hereinafter. For example, although the mounting cone and base assembly is illustrated as being used to assemble the sleeve and constrictor ring prior to use of the apparatus. The cone may also serve the dual function of a testing expedient for checking the operability of the pump unit 14. This dual function may be carried out by inserting the mounting cone 22 into the tube 12 when the pump unit is arranged as shown in FIG. 1, and operating the pump unit to create a vacuum in the tube. While this is done, the cone serves as a closure member which prevents the admission of air into the tube 12. This alternate use of the mounting cone is also useful in demonstrating the operation of the apparatus to a potential user thereof.

I claim:

1. A compact vacuum therapy system for assisting a male erection comprising:
    a tube presenting a first end sized for receiving a human penis therein and a second end;
    a pump body detachably mountable to said second end of said tube in air-sealing relationship, and presenting an intake end in fluidic communication with said tube;
    a piston axially reciprocal within said pump body; and
    a sealing member positioned in said pump body, said piston including a circumscribing groove sized for receiving said sealing member therein, said groove being sized relative to said sealing member so as to permit shifting of said sealing member in an axial direction within said groove, said groove including a forward wall section and a rear wall section, said rear wall section including structure defining at least one opening therein, said groove being configured to present an axially oriented air passageway extending rearwardly from said front wall and located between said piston and said sealing member.

2. A compact vacuum therapy system as set forth in claim 1, said piston including a regulator for limiting the vacuum within said system.

3. A compact vacuum therapy system as set forth in claim 1, including a manually actuatable relief valve fluidically connected to said tube.

4. A compact vacuum therapy system as set forth in claim 1, said piston being reciprocal along a first axis, said tube being mountable on said pump body in substantially a common axis with said first axis.

5. A compact vacuum therapy system as set forth in claim 1, including a return spring operably connected to said piston.

6. A compact vacuum therapy system for assisting a male erection comprising:
    a tubular member sized for receiving a penis therein; and
    a pump unit for evacuating said tubular member, said pump unit including a pump body presenting a first piston-receiving end and a second, axially opposed intake end, said pump body including structure for alternately mounting one of said piston-receiving end or said intake end interior to said tube.

7. A compact vacuum therapy system as set forth in claim 6, including an axially reciprocable manually-actuatable piston, said piston having a portion thereof located within said piston-receiving end and a shaft extending externally of said pump body.

8. A compact vacuum therapy system as set forth in claim 7, including a vacuum overload regulator positioned internally to said piston.

9. A compact vacuum therapy system as set forth in claim 6, including a rim located intermediate said piston-receiving end and said intake end for abutment with said tubular member when mounted to said pump body.

* * * * *